(12) United States Patent
Barrett

(10) Patent No.: US 10,294,103 B2
(45) Date of Patent: May 21, 2019

(54) IMPROVEMENTS RELATING TO HYPOCHLOROUS ACID SOLUTIONS

(71) Applicant: XANADOX TECHNOLOGIES LIMITED, Daventry Northamptonshire (GB)

(72) Inventor: Richard Maxwell Barrett, Daventry (GB)

(73) Assignee: XANADOX TECHNOLOGIES LIMITED, Daventry Northamptonshire (GB)

( * ) Notice: Subject to any disclaimer, the term of this patent is extended or adjusted under 35 U.S.C. 154(b) by 53 days.

(21) Appl. No.: 15/524,979

(22) PCT Filed: Nov. 9, 2015

(86) PCT No.: PCT/GB2015/053387
§ 371 (c)(1),
(2) Date: May 5, 2017

(87) PCT Pub. No.: WO2016/071720
PCT Pub. Date: May 12, 2016

(65) Prior Publication Data
US 2018/0282160 A1  Oct. 4, 2018

(30) Foreign Application Priority Data

Nov. 7, 2014  (GB) .................................. 1419901.2

(51) Int. Cl.
| | | |
|---|---|---|
| *A61L 2/00* | (2006.01) | |
| *A61L 2/18* | (2006.01) | |
| *C01B 11/04* | (2006.01) | |
| *A61K 33/00* | (2006.01) | |

(52) U.S. Cl.
CPC .............. *C01B 11/04* (2013.01); *A61K 33/00* (2013.01); *A61L 2/0088* (2013.01); *A61L 2/18* (2013.01)

(58) Field of Classification Search
CPC ......... C01B 11/04; A01N 59/00; A61K 33/00; A61L 2/0088; A61L 2/18
See application file for complete search history.

(56) References Cited

U.S. PATENT DOCUMENTS

| | | | |
|---|---|---|---|
| 1,481,003 A | | 1/1924 | Gegenheimer |
| 2,166,363 A | | 7/1939 | MacMahon |
| 2,199,936 A | * | 5/1940 | Kauffmann ............. C01B 11/04 252/187.28 |
| 2,829,110 A | * | 4/1958 | Robson ................ C11D 3/3953 252/187.29 |
| 5,118,426 A | | 6/1992 | Duncan et al. |
| 6,984,398 B2 | | 1/2006 | Brennan et al. |
| 2004/0226894 A1 | | 11/2004 | Okazaki |
| 2010/0112092 A1 | | 5/2010 | Northey |
| 2010/0272830 A1 | | 10/2010 | Faita |

FOREIGN PATENT DOCUMENTS

| | | |
|---|---|---|
| EP | 1781567 B1 | 10/2013 |
| JP | 2004337582 A | 12/2004 |
| KR | 20120129333 A | 11/2012 |
| WO | 2010/148004 A1 | 12/2010 |
| WO | 2012/123695 A2 | 9/2012 |
| WO | WO-2012123695 A2 * | 9/2012 ............. A01N 25/34 |

OTHER PUBLICATIONS

International Search Report and Written Opinion for International Application No. PCT/GB2015/053387, dated May 24, 2016 (14 pages).

* cited by examiner

Primary Examiner — Mark V Stevens
(74) Attorney, Agent, or Firm — Kagan Binder, PLLC

(57) ABSTRACT

A process for preparing an aqueous solution comprising hypochlorous acid, the process comprising: (i) treating an aqueous starting solution comprising hypochlorite and a precipitable counter-ion with a precipitation agent to form a counter-ion precipitate and a supernatant liquid having a pH greater than 6; (ii) removing at least part of said precipitate; and subsequently (iii) acidifying at least part of the supernatant liquid with a strong inorganic acid other than hydrochloric acid, to a pH in the range of from 3.0 to 6.0, to form an aqueous product solution comprising hypochlorous acid. Solutions obtainable by the process are also described, as are related uses.

12 Claims, No Drawings

IMPROVEMENTS RELATING TO HYPOCHLOROUS ACID SOLUTIONS

FIELD OF THE INVENTION

This invention relates to solutions comprising hypochlorous acid. In particular, though not exclusively, this invention relates to processes for preparing aqueous solutions comprising hypochlorous acid, aqueous solutions obtainable thereby, and related uses.

BACKGROUND TO THE INVENTION

Adding chlorine ($Cl_2$) to water via the addition of chlorine gas or hypochlorites is a well-established method of treating water to reduce the level of microbes. Microbiologically contaminated surfaces and water remain a major source of infection resulting in a significant amount of death and illness, particularly in environments such as hospitals where patients are vulnerable due to lowered or compromised immunity. The use of sterilizing and disinfecting solutions which can help to reduce of pathogens on surfaces, or help to provide water free from harmful pathogens, can greatly reduce infection rates.

When dissolved in water, chlorine dissociates to an equilibrium of chlorine ($Cl_2$), hypochlorous acid (HOCl) and hydrochloric acid (HCl). In acidic solutions, the major species are $Cl_2$ and HOCl whereas in alkali solutions the equilibrium favours the hypochlorite ion ($OCl^-$).

The efficacy of HOCl is known to be greater than $OCl^-$, due to faster penetration though the microbial cell wall, meaning that acidic solutions containing more hypochlorous acid provide greater efficacy than alkali solutions containing more negatively charged hypochlorite ions.

Alkali hypochlorite solutions, which are commonly referred to as bleach, are widely used to disinfect surfaces due to their broad availability and low cost. However, the high pH required to maintain stability of these solutions results in predominantly hypochlorite ions rather than hypochlorous acid being present in the solutions.

When used to chlorinate drinking water, the lower efficacy of alkali solutions may result in more hypochlorite being added to the water than would be necessary to obtain adequate disinfection if hypochlorous acid were present. The addition of such alkali products can also increase the pH and lead to increased scale generation.

Hypochlorous acid solutions may be produced by electrolytic processes, but the resulting solutions contain high levels of chloride ions, resulting in poor storage stability and pH fluctuations with time. This route therefore has limited use, and is most suited to on site generation and low volumes of product.

A further known approach is to acidify solutions of hypochlorite to obtain solutions of hypochlorous acid. However, this is not straightforward. Solutions of hypochlorous acid produced by the acidification of hypochlorite solutions are inherently unstable. Hypochlorous acid solutions will degrade according to the environmental factors of (i) temperature (ii) ultraviolet radiation; and (iii) concentration of chloride ion ($Cl^-$) in solution.

Chloride ions in hypochlorite solutions may in particular stem from hypochlorite salts used to make those solutions. The electrolysis of brine to produce hypochlorite salts, e.g. calcium or sodium hypochlorite, generally leads to the presence of substantial levels of chloride ($Cl^-$).

The stability of hypochlorous acid solutions can be extended by the addition of stabilisers such as dimethyl hydantoin. However, this works principally via the generation of complexes, which are less efficacious than free halogens such as HOCl.

WO2012/123695 describes a process for preparing a stable aqueous solution of hypochlorous acid which involves adding calcium hypochlorite to water (preferably deionised), manipulating the chloride levels in the resulting solution to be at a maximum of 1 chloride: 3 hypochlorous acid and controlling the pH of the solution to between 3.5 to 7.0 by using phosphoric acid. The resulting solution is shown to have an 80% retention in HOCl over one month.

A need remains for an improved process for preparing aqueous solutions comprising hypochlorous acid, for example resulting in more stable solutions and/or improved ease of production.

STATEMENTS OF THE INVENTION

According to a first aspect of the invention there is provided a process for preparing an aqueous solution comprising hypochlorous acid, the process comprising:
(i) treating an aqueous solution comprising hypochlorite and a precipitable counter-ion with a precipitation agent to form a counter-ion precipitate and a supernatant liquid having a pH greater than 6;
(ii) removing at least part of said precipitate; and subsequently
(iii) acidifying at least part of the supernatant liquid with a strong inorganic acid other than hydrochloric acid, to a pH in the range of from 3.0 to 6.0, to form an aqueous solution comprising hypochlorous acid.

It has been found that the process according to the first aspect of the invention can provide a low pH aqueous solution comprising hypochlorous acid, having a high redox potential, a low chloride content and good stability.

Advantageously, the process may facilitate the manufacture of solutions in large volumes, and/or using a range of inorganic acids.

It has surprisingly been found that, in embodiments of the invention, the aqueous solution comprising hypochlorite and a precipitable counter-ion may comprise chloride impurities without substantially affecting the advantageous results. For example, it has been found that aqueous solutions produced from mains water rather than deionised water may be readily employed. This is of great benefit in industrial scale up and for use in developing regions.

Unlike in prior art such as WO2012/123695 where acidification and precipitation are linked and occur concurrently, in the process according to the first aspect of the invention the pH can be determined independently of precipitation. Also, conversely, precipitation is not dependent on acidification. This facilitates the production of solutions for different purposes, such as for example use in surface disinfection or in the chlorination of water for antimicrobial purposes.

For brevity, and without implying any limitation, the solution comprising hypochlorite and a precipitable counter-ion will hereinafter be referred to as "starting solution", whilst the prepared aqueous solution comprising hypochlorous acid will be referred to as "product solution".

The starting solution may be of any suitable type. Conveniently, the starting solution may comprise or consist of a hypochlorite salt component dissolved in an aqueous medium. The process may comprise dissolving the hypochlorite salt component in the aqueous medium to form the starting solution.

In an embodiment, the hypochlorite salt component comprises at least one of calcium hypochlorite and magnesium hypochlorite. Advantageously, the hypochlorite salt component may comprise calcium hypochlorite. The hypochlorite salt component may advantageously comprise or consist of a commercial grade hypochlorite, in particular commercial grade calcium hypochlorite. The commercial grade hypochlorite may suitably have an assay purity of at least 60% w/w, in particular at least 70% w/w, such as at least 75% w/w.

Due the nature of manufacturing processes, commercial grade calcium hypochlorite tends to contain a lower level of chloride impurities than commercial grade sodium hypochlorite. Low chloride levels may aid stability of the product solution. Whilst prior art product solutions derived from calcium hypochlorite may suffer from undesirable cloudiness or precipitation, this can be overcome by aspects of the present invention thanks to treatment of the starting solution with the precipitation agent (e.g. sodium carbonate).

In an embodiment, the hypochlorite salt component comprises at most 15% w/w chloride (e.g. calcium chloride and sodium chloride), in particular at most 10% w/w chloride, such as at most 5% w/w chloride. The chlorine content of the hypochlorite salt component may on occasion be at least 1% w/w, such as at least 2% w/w, or even at least 3% w/w.

The starting solution may thus comprise at least one of calcium and magnesium hypochlorite, in particular calcium hypochlorite. For the avoidance of doubt, magnesium and/or calcium are examples of precipitable counter-ions in aqueous solution.

The concentration of hypochlorite in the starting solution may be chosen consistent with a desired free chlorine content in the product solution. Suitably, the amount of hypochlorite salt in the starting solution may be in the range of from 0.5 mM (mmol/L) to 0.5 M (mol/L), in particular in the range of from 0.1 mM to 0.2 M, such as in the range of from 0.2 mM to 0.1 M. Suitable concentrations may also be calculated from the Examples herein.

The aqueous medium comprises water. Advantageously, the aqueous medium may be deionized water. However, in some embodiments of the invention, the aqueous medium need not be deionized. For example, the aqueous medium may comprise at least 30 ppm chloride, in particular in the range of from 30 to 500 ppm chloride, such as in the range of from 50 to 100 ppm chloride. Advantageously, the aqueous medium may comprise or consist of mains water.

The starting solution is treated to form a counter-ion precipitate and a supernatant liquid having a pH greater than 6.

The starting solution is treated with a precipitation agent suitable for forming a counter-ion precipitate and a hypochlorite-containing supernatant liquid. Advantageously, the precipitation agent may be a water-soluble salt. The precipitation agent may, for example, comprise an alkali metal carbonate.

In an embodiment, the starting solution is treated with an alkali metal carbonate to form a carbonate counter-ion precipitate and a supernatant liquid comprising alkali metal hypochlorite. Carbonate precipitates may precipitate more readily and be more easily separable than other precipitates, such as phosphates.

For example, where the starting solution comprises calcium hypochlorite, treatment with an alkali metal carbonate leads to the formation of a calcium carbonate precipitate, which can be readily removed by settling and/or filtration. The supernatant liquid then comprises an aqueous solution of alkali metal hypochlorite.

The alkali metal carbonate may suitably comprise sodium and/or potassium carbonate. Conveniently, the alkali metal carbonate may be sodium carbonate.

The starting solution may be treated with the alkali metal carbonate or other precipitation agent in any suitable manner, in particular by mixing the carbonate with the starting solution. In an embodiment, the treatment comprises adding an amount of carbonate or other precipitation agent to the starting solution and agitating the resultant mixture.

The amount of alkali metal carbonate or other precipitation agent may advantageously be chosen in dependence on the amount of counter-ion in the aqueous solution. Thus the process may comprise treating the starting solution with at least a stoichiometric amount of alkali metal carbonate or other precipitation agent. However, other amounts may also be used in principle.

At least part of the precipitate is removed before the supernatant liquid is acidified. Without wishing to be bound by theory, it may be that the stability observed in the product solution is enhanced by this separation of precipitation and acidification.

Advantageously, the process may comprise removing substantially all the precipitate before acidification below pH 6. In an embodiment, at least 80% w/w, preferably at least 90% w/w, even more preferably at least 95% w/w of the precipitate is removed.

The precipitate may be removed in any suitable manner. For example, the process may comprise: allowing the precipitate to settle, pumping away a slurry comprising the settled precipitate; and optionally filtering the precipitate from the slurry. The slurry may be filtered, for example, by in-line bag filtration in conventional fashion to obtain the precipitate.

At least part of the supernatant liquid is acidified with a strong inorganic acid other than hydrochloric acid, to a pH in the range of from 3.0 to 6.0, to form the product solution. Hydrochloric acid is not used because chloride anions ($Cl^-$) would make the product solution unstable. In an embodiment, the strong inorganic acid comprises at least one of nitric acid ($HNO_3$), sulphuric acid ($H_2SO_4$) and phosphoric acid ($H_3PO_4$). In an embodiment, the strong inorganic acid comprises, or consists of, sulphuric acid.

In an embodiment, the supernatant liquid is acidified to a pH in the range of from 3.0 to 4.5, or in the range of from 3.0 to 4.0, or in the range of from 3.0 to 3.5. In an embodiment, the supernatant liquid is acidified to a pH in the range of from 3.2 to 6.0, in the range of from 3.2 to 4.5, in the range of from 3.2 to 4.0, or in the range of from 3.2 to 3.5.

The process may of course be tailored to obtain a desired product solution. For example, as aforesaid, the concentration of hypochlorite in the starting solution may be chosen consistent with a desired free chlorine content in the product solution.

The invention also embraces, according to a second aspect of the invention an aqueous solution comprising hypochlorous acid (i.e. the product solution) obtainable by the process of the first aspect of the invention.

In an embodiment, the free chlorine content in the product solution may be in the range of from 25 ppm to 10000 ppm, such as in the range of from 250 to 8000 ppm.

In some embodiments the product solution has a free chlorine content in the range of from 100 to 1000 ppm. In some embodiments the product solution has a free chlorine content in the range of from 500 to 1500 ppm. In some embodiments the product solution has a free chlorine content in the range of from 1500 to 3500 ppm. In some embodiments the product solution has a free chlorine content in the range of from 2000 to 4500 ppm. In some embodiments the product solution has a free chlorine content in the range of from 3000 to 5500 ppm. In some embodiments the product solution has a free chlorine content in the range of from 4000 to 6000 ppm.

Unless stated otherwise, free chlorine is measured herein according to the method specified in BS 1427:1962 and amendment 3:1968, based on N,N-Diethyl-p-phenylene diamine (DPD) reagent. High concentrations of free chlorine can be measured by diluting such that the anticipated range falls within one of the standard Lovibond® discs within the 3/40 series. Specifically, a DPD 1 tablet is crushed and dissolved in a 10 ml diluted sample (dilution factor F noted) within a 13.5 mm moulded cell. A blank sample is then placed into another 13.5 mm moulded cell and a comparison reading is read off the 3/40 disc when the colours equate against a white light background. This reading is then multiplied by F to give the actual free chlorine within the sample.

The product solution may be a solution with a given stability. The invention embraces, also from a third aspect, an aqueous solution comprising hypochlorous acid, such as for example a product solution as defined anywhere hereinabove, being capable of one or more of:

retaining at least 70% w/w of free chlorine after at least 3 months, preferably at least 6 months, or even at least 12 months of dark storage at 20 degrees Celsius.

retaining at least 80% w/w of free chlorine after at least 3 months, preferably at least 6 months, or even at least 12 months of dark storage at 20 degrees Celsius retaining at least 95% w/w oxidation/reduction potential after at least 3 months, preferably at least 6 months, or even at least 12 months of dark storage at 20 degrees Celsius maintaining a pH within plus/minus 0.5 after at least 3 months, preferably at least 6 months, or even at least 12 months of dark storage at 20 degrees Celsius.

According to a fourth aspect of the invention there is provided a process for modifying an aqueous solution comprising hypochlorous acid, the process comprising: (a) treating an aqueous solution comprising hypochlorous acid with lead nitrate, to form a lead-based precipitate; and (b) removing at least a part of said lead-based precipitate to obtain a modified aqueous solution comprising hypochlorous acid.

It has been found that such a method results in more stable hypochlorous acid solutions with surprisingly high ORP levels.

The fourth aspect of the invention may advantageously be used in combination with the first aspect of the invention. In particular, the first aspect of the invention may comprise treating the product solution with lead nitrate, to form a lead-based precipitate; and (b) removing at least a part of said lead-based precipitate to obtain a modified aqueous solution comprising hypochlorous acid.

According to a fifth aspect of the invention there is provided a process for preparing an aqueous solution comprising hypochlorous acid, the process comprising:
(i) treating an aqueous (starting) solution comprising calcium or magnesium hypochlorite with an alkali metal carbonate to form a precipitate and a supernatant liquid;
(ii) removing at least part of said precipitate; and subsequently
(iii) acidifying at least part of the supernatant liquid with a strong inorganic acid other than hydrochloric acid, to a pH in the range of from 3.0 to 6.0, to form an aqueous (product) solution comprising hypochlorous acid.

Optional and preferred aspects of the fifth aspect may be as described in respect of the first aspect of the invention.

From a sixth aspect, the invention resides in the use of an aqueous (product) solution comprising hypochlorous acid according to any aspect or embodiment of the invention as an antimicrobial or disinfectant. In an embodiment, the use comprises storing the solution for a period of at least one week, suitably at least one month, or even at least three months. In particular, the use may comprise contacting the solution with microbes, or disinfecting a substrate with the solution, after a period of at least one week, suitably at least one month, or even at least three months of storage.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, then a range of values defined by a combination of any of the upper limits with any of the lower limits may also be implied. In this specification, references to compound properties are—unless stated otherwise—to properties measured under ambient conditions, i.e. at atmospheric pressure and at a temperature of about 20° C.

EXAMPLES

Example 1—Production of Hypochlorous Acid Solutions

Calcium hypochlorite is commercially available in a low chloride (LC) form as high test hypochlorite (HTH), which typically has an assay purity of at least 65% w/w and in an ultra low chloride (ULC) form (e.g. Lonza SHOCK) having an assay purity of at least 78% and a chloride of less than 5% w/w.

This example describes how sodium hypochlorite solutions can readily be produced from a solution of calcium hypochlorite by the addition of sodium carbonate ($Na_2CO_3$). The method involves dissolution of calcium hypochlorite in mains water which generates an alkali calcium hypochlorite solution. The hydrolysis performed by the hypochlorite ion as hypochlorous acid is weak, but calcium hydroxide is a strong base. Particularly where ULC calcium hypochlorite is used, this basic solution is low in chloride due to the low chloride content of the calcium hypochlorite (e.g. less than 5.0% w/w). The addition of sodium carbonate to this basic solution results in the generation of calcium carbonate and a basic solution of hypochlorite.

$$Ca^{2+}(OCl^-)_2 + (Na^+)_2CO_3^{2-} \rightarrow CaCO_3 + 2(Na^+OCl^-)$$

A fine white insoluble calcium carbonate precipitate is formed which readily settles after a few hours to the bottom of the reaction vessel. The clear supernatant liquid, a basic solution of low chloride containing hypochlorite, can then be filtered, for example in the laboratory with a Whatman No. 1 filter disc or on a larger scale production through a 1 micron bag filter.

The resulting solution of ultra low chloride (ULC) sodium hypochlorite can then be acidified with an inorganic acid to produce hypochlorous acid solutions.

$$Na^+OCl^- + H^+X^- = HOCl + Na^+X^-$$

The concentrations of calcium hypochlorite used are shown in Table 1.

TABLE 1

| | gm per 1 litre of water | |
|---|---|---|
| | Calcium Hypochlorite (ULC) | Calcium Hypochlorite (LC) |
| XANADOX 10,000 | 17.40 | 20.00 |
| XANADOX 8,000 | 14.00 | 16.00 |
| XANADOX 6,000 | 10.50 | 12.00 |
| XANADOX 5,000 | 8.70 | 10.00 |
| XANADOX 4,000 | 7.00 | 8.00 |
| XANADOX 2,500 | 4.40 | 5.00 |
| XANADOX 2,000 | 3.50 | 4.00 |
| XANADOX 1,000 | 1.75 | 2.00 |
| XANADOX 500 | 0.88 | 1.00 |
| XANADOX 250 | 0.44 | 0.50 |

Experiments have been conducted over many months on the preparation and stability characteristics of hypochlorous acid solutions prepared by the precipitation of calcium carbonate and acidification to an optimum pH point.

In each experiment, the following analytical tests were carried out at periodic intervals:

(1) ORP (Oxidation reduction potential—mV)—A Delta Ohm meter (Model HD 3405.2) with ORP electrode and temperature compensation probe (Supplied by LTH Electronics, Luton, Beds UK) was used in permanent ORP mode & calibrated for temperature on a daily basis. The electrode was then inserted into a 650 mV Redox standard solution and after 5 minutes the reading was noted. The difference in readings from the standard 650 mV was noted and applied as a correction to all the redox readings measured on the day. After removing the electrode from the redox standard 650 mV solution, it was thoroughly rinsed in DI water before a ORP measurement was taken.

(2) pH—A Hanna Instruments HI 2209 pH meter was used permanently in pH mode & calibrated for temperature on a daily basis. The electrode was inserted into standard pH 4 and 7 solutions and calibrated on a daily basis. The electrode was then placed into the experimental solutions and the pH reading noted.

(3) [$Cl_2$] concentration of free chlorine—Method is specified in BS 1427:1962 and amendment 3:1968. Based on the reaction of free chlorine reacting with N,N-Diethyl-p-phenylene diamine to produce a red colour. In comparative studies by the Water Research Association (Tech. Papers Nos. 29:1963, 47:1965 and 53:1966) it was concluded that the Palin-DPD procedure was the best then available for the determination of free chlorine and chloramines (addition of potassium iodide) in water. High concentrations of free chlorine can be measured by diluting such that the anticipated range falls within one of the standard Lovibond® discs within the 3/40 series. Specifically, a DPD 1 tablet is crushed and dissolved in a 10 ml diluted sample (dilution factor F noted) within a 13.5 mm moulded cell. A blank sample is then placed into another 13.5 mm moulded cell and a comparison reading is read off the 3/40 disc when the colours equate against a white light background. This reading is then multiplied by F to give the actual free chlorine within the sample. In some experiments the concentration of free chlorine was measured by an alternative but equivalent titration method.

1A. Preparation of Sample Solutions of XANADOX 5000

A graduated 5 liter beaker was filled with 4.5 liters of water and 40 gm of SHOCK (Calcium hypochlorite ULC grade—Lonza Inc) was slowly added. Stirring was effected with a magnetic stirrer until a cloudy white dispersion appeared evenly distributed, and no solid material on the base of the container.

30 gm of sodium carbonate (Alfa Aesar, anhydrous 99.5% purity, chloride 0.001%) was added slowly with stirring. A white calcium carbonate precipitate was produced. The magnetic stirrer was switched off and the calcium carbonate was allowed to settle to the bottom of the beaker. After approx. two hours the clear supernatant liquid was filtered through a 1 micron filter bag.

The resulting clear solution was poured into four 1000 ml HD polythene sample bottles. Each 1000 ml aliquot was added to a 1500 ml beaker with a magnetic stirrer. A pH probe (connected to a pH meter) was suspended in the 1000 ml sodium hypochlorite solution.

50% Sulphuric acid (Analar Normapur) was carefully added by drop pipette to four of the 1000 ml aliquots with the aim of achieving the following pH readings—5.7, 5.0, 4.5, 4.0.

Table 2 gives the addition of 50% sulphuric acid to achieve the desired pH values.

Mixed bed deionised water was used to make XANADOX 5000 samples 230-233.

TABLE 2

| | SAMPLE NO. | | | |
|---|---|---|---|---|
| | 230 | 231 | 232 | 233 |
| 50% sulphuric acid added (gm) | 11.9 | 12.2 | 12.4 | 12.4 |
| Initial pH achieved | 5.68 | 5.03 | 4.53 | 3.90 |

The acidified solutions were then transferred to the 1000 ml HD polythene bottles and sealed with closures. The solutions were stored away from sunlight at ambient temperature in a cool warehouse storeroom.

Table 3 below charts the change in ORP, pH and oxidant concentration over a 19 month period following DATE OF PRODUCTION 21 Jul. 2012.

TABLE 3

| | | DATE | | | | |
|---|---|---|---|---|---|---|
| | | 23 Oct. 2012 | 12 Feb. 2013 | 14 Sep. 2013 | 4 Feb. 2014 | 12 Aug. 2014 |
| 230 | ORP | 1233 | 1242 | 1259 | 1241 | 1242 |
| | pH | 3.39 | 3.27 | 3.17 | 3.16 | 2.90 |
| | [$Cl_2$] | 5601 | 5170 | 4254 | 3970 | 3260 |
| 231 | ORP | 1234 | 1235 | 1258 | 1237 | 1260 |
| | pH | 3.08 | 3.24 | 3.17 | 3.17 | 3.01 |
| | [$Cl_2$] | 5601 | 5524 | 4325 | 4041 | 3403 |
| 232 | ORP | 1219 | 1239 | 1256 | 1253 | 1267 |
| | pH | 3.27 | 3.12 | 2.90 | 2.88 | 2.79 |
| | [$Cl_2$] | 5814 | 5241 | 4325 | 4041 | 3261 |
| 233 | ORP | 1237 | 1237 | 1262 | 1254 | 1267 |
| | pH | 3.01 | 3.13 | 3.00 | 2.87 | 2.76 |
| | [$Cl_2$] | 5956 | 5524 | 4609 | 4325 | 3687 |

The above results show that over a 24 month period, the solution that has been acidified to near pH 4.0 shows the greater stability in free chlorine, with a good ORP.

1B. Preparation of Sample Solutions of XANADOX 2500

A graduated 5 liter beaker was filled with 4.5 liters of water and 20 gm of SHOCK (Calcium hypochlorite ULC grade—Lonza Inc) was slowly added. Stirring was effected with a magnetic stirrer until a cloudy white dispersion appeared evenly distributed, and no solid material on the base of the container.

15 gm of sodium carbonate (Alfa Aesar, anhydrous 99.5% purity, chloride 0.001%) was added slowly with stirring. A white calcium carbonate precipitate was produced. The magnetic stirrer was switched off and the calcium carbonate was allowed to settle to the bottom of the beaker. After approx., two hours the clear supernatant liquid was filtered through a 1 micron filter bag.

The resulting clear solution was poured into four 1000 ml HD polythene sample bottles. Each 1000 ml aliquot was added to a 1500 ml beaker with a magnetic stirrer. A pH probe (connected to a pH meter) was suspended in the 1000 ml sodium hypochlorite solution.

50% Sulphuric acid (Analar Normapur) was carefully added by drop pipette to four of the 1000 ml aliquots with the aim of achieving the following pH readings—5.7, 5.0, 4.5, 4.0.

Table 4 gives the addition of 50% sulphuric acid to achieve the desired pH values.

Mixed bed deionised water was used to make XANADOX 2500 samples 234-237.

TABLE 4

| | SAMPLE NO. | | | |
|---|---|---|---|---|
| | 234 | 235 | 236 | 237 |
| 50% sulphuric acid added (gm) | 5.9 | 6.3 | 6.2 | 6.1 |
| Initial pH achieved | 5.72 | 5.05 | 4.45 | 3.85 |

The acidified solutions were then transferred to the 1000 ml HD polythene bottles and sealed with closures. The solutions were stored away from sunlight at ambient temperature in a cool Table 5 below charts the change in ORP, pH and oxidant concentration over a 19 month period following DATE OF PRODUCTION 23 Jul. 2012.

TABLE 5

| | | DATE | | | |
|---|---|---|---|---|---|
| | | 23 Oct. 2012 | 1 Oct. 2013 | 4 Feb. 2014 | 12 Aug. 2014 |
| 234 | ORP | 1217 | 1241 | 1217 | 1239 |
| | pH | 3.43 | 3.29 | 3.55 | 3.30 |
| | [Cl$_2$] | 3332 | 2694 | 2552 | 2233 |
| 235 | ORP | 1217 | 1244 | 1232 | 1253 |
| | pH | 3.37 | 3.20 | 3.21 | 2.98 |
| | [Cl$_2$] | 3261 | 2907 | 2623 | 2127 |
| 236 | ORP | 1221 | 1249 | 1233 | 1246 |
| | pH | 3.30 | 3.09 | 3.19 | 3.12 |
| | [Cl$_2$] | 3474 | 2907 | 2765 | 2446 |
| 237 | ORP | 1219 | 1246 | 1235 | 1248 |
| | pH | 3.29 | 3.11 | 3.16 | 3.06 |
| | [Cl$_2$] | 3474 | 2978 | 2765 | 2552 |

The above results show that over a 24 month period, that the solution that has been acidified to near pH 4.0 shows the greater stability with a good ORP.

1C. Preparation of Sample Solutions of XANADOX 8000

Experiments were conducted to ascertain the medium and long term stability of high concentration (8000 ppm) hypochlorous acid solutions. Both mixed bed quality deionised water (nil chloride content) and Daventry towns mains water (approx. 80 ppm as Cl$^-$]) were used to assess relative stability.

A graduated 5 liter beaker was filled with 4.5 liters of water and 64 gm of SHOCK (Calcium hypochlorite ULC grade—Lonza Inc) was slowly added. Stirring was effected with a magnetic stirrer until a cloudy white dispersion appeared evenly distributed, and no solid material on the base of the container.

48 gm of sodium carbonate (Alfa Aesar, anhydrous 99.5% purity, chloride 0.001%) was added slowly with stirring. A white calcium carbonate precipitate was produced. The magnetic stirrer was switched off and the calcium carbonate was allowed to settle to the bottom of the beaker. After approx. two hours the clear supernatant liquid was filtered through a 1 micron filter bag.

The resulting clear solution was poured into eight 500 ml HD polythene sample bottles. Each 500 ml aliquot was added to a 1000 ml beaker with a magnetic stirrer. A pH probe (connected to a pH meter) was suspended in the 500 ml sodium hypochlorite solution.

98% Sulphuric acid (Analar Normapur) was carefully added by drop pipette to four of the 500 ml aliquots with the aim of achieving the following pH readings—6.0, 5.5, 5.0, 4.5.

81% Phosphoric acid (FG—Food Grade) was added carefully by drop pipette to the remaining four 500 ml aliquots with the aim of achieving the following pH readings—6.0, 5.5, 5.0, 4.5.

Daventry Towns Mains water was used to make samples 570-577.

Table 6 gives the addition of 98% sulphuric acid and 81% phosphoric acid to achieve the desired pH values.

TABLE 6

| | SAMPLE NO. | | | |
|---|---|---|---|---|
| | 570 | 571 | 572 | 573 |
| 98% sulphuric acid added (gm) | 3.96 | 3.99 | 4.09 | 4.17 |
| Initial pH achieved | 6.00 | 5.50 | 4.60 (*) | 3.06 (*) |
| | SAMPLE NO. | | | |
| | 574 | 575 | 576 | 577 |
| 81% phosphoric acid added (gm) | 7.55 | 9.00 | 10.03 | 11.08 |
| Initial pH achieved | 6.00 | 5.50 | 5.0 | 4.50 |

(*) acid addition overshot desired pH value.

The acidified solutions were then transferred to the 500 ml HD polythene bottles and sealed with closures. All eight solutions were stored away from sunlight at ambient temperature in a cool warehouse storeroom.

Table 7 below charts the change in ORP, pH and oxidant concentration since DATE OF PRODUCTION 16 Oct. 2013.

TABLE 7

| | Sample No. | | | | | | | |
|---|---|---|---|---|---|---|---|---|
| | 570 | 571 | 572 | 573 | 574 | 575 | 576 | 577 |
| DATE 21 Oct. 2013 Towns Mains Water | | | | | | | | |
| ORP | 1257 | 1254 | 1252 | 1264 | 1225 | 1230 | 1227 | 1222 |
| pH | 3.36 | 3.29 | 3.26 | 3.04 | 3.71 | 3.60 | 3.62 | 3.60 |
| [$Cl_2$] | 9217 | 9713 | 10068 | 10210 | 7586 | 8863 | 9430 | 9430 |
| DATE 25 Nov. 2013 Towns Mains Water | | | | | | | | |
| ORP | 1235 | 1235 | 1237 | 1242 | 1217 | 1225 | 1226 | 1225 |
| pH | 3.43 | 3.36 | 3.33 | 3.22 | 3.65 | 3.51 | 3.47 | 3.47 |
| [$Cl_2$] | 8295 | 8863 | 9146 | 9288 | 6806 | 8012 | 8508 | 8579 |
| DATE 28 Jan. 2014 Towns Mains Water | | | | | | | | |
| ORP | 1261 | 1253 | 1253 | 1256 | 1228 | 1237 | 1242 | 1240 |
| pH | 3.33 | 3.31 | 3.26 | 3.21 | 3.57 | 3.47 | 3.43 | 3.44 |
| [$Cl_2$] | 7515 | 8083 | 8154 | 8508 | 6097 | 7019 | 7586 | 7657 |
| DATE 28 Mar. 2014 Towns Mains Water | | | | | | | | |
| ORP | 1243 | 1245 | 1246 | 1248 | 1221 | 1232 | 1235 | 1233 |
| pH | 3.20 | 3.17 | 3.13 | 3.08 | 3.50 | 3.34 | 3.27 | 3.28 |
| [$Cl_2$] | 6877 | 7445 | 7728 | 8012 | 5530 | 6452 | 6948 | 7161 |

Mixed bed deionised water was used to make samples 580-587.

Table 8 gives the addition of 98% sulphuric acid and 81% phosphoric acid to achieve the desired pH values.

TABLE 8

| | SAMPLE NO. | | | | | | | |
|---|---|---|---|---|---|---|---|---|
| | 580 | 581 | 582 | 583 | 584 | 585 | 586 | 587 |
| 98% sulphuric acid added (gm) | 4.06 | 4.24 | 4.44 | 4.45 | | | | |
| Initial pH achieved | 6.00 | 5.50 | 4.79 (*) | 3.53 (*) | | | | |
| 81% phosphoric acid added (gm) | | | | | 8.06 | 9.33 | 10.54 | 10.86 |
| Initial pH achieved | | | | | 6.00 | 5.50 | 4.16 (*) | 3.64(*) |

(*) acid addition overshot desired pH value.

Table 9 below charts the change in ORP, pH and oxidant concentration since DATE OF PRODUCTION 16 Oct. 2013.

TABLE 9

| | Sample No. | | | | | | | |
|---|---|---|---|---|---|---|---|---|
| | 580 | 581 | 582 | 583 | 584 | 585 | 586 | 587 |
| DATE 21 Oct. 2013 Mixed Bed Deionised Water | | | | | | | | |
| ORP | 1226 | 1230 | 1227 | 1231 | 1197 | 1202 | 1210 | 1214 |
| pH | 3.46 | 3.38 | 3.33 | 3.26 | 3.88 | 3.71 | 3.55 | 3.48 |
| [$Cl_2$] | 9004 | 9572 | 9855 | 10068 | 7161 | 8508 | 9713 | 9855 |
| DATE 28 Jan. 2014 Mixed Bed Deionised Water | | | | | | | | |
| ORP | 1245 | 1250 | 1253 | 1254 | 1227 | 1236 | 1244 | 1246 |
| pH | 3.42 | 3.32 | 3.28 | 3.24 | 3.62 | 3.52 | 3.40 | 3.36 |
| [$Cl_2$] | 7161 | 7799 | 8224 | 8295 | 5601 | 6806 | 7799 | 8083 |
| DATE 31 Mar. 2014 Mixed Bed Deionised Water | | | | | | | | |
| ORP | 1263 | 1265 | 1267 | 1268 | 1236 | 1246 | 1254 | 1255 |
| pH | 3.16 | 3.09 | 3.03 | 3.03 | 3.48 | 3.32 | 3.22 | 3.19 |
| [$Cl_2$] | 6736 | 7232 | 7657 | 7799 | 5388 | 6239 | 7161 | 7374 |

1D. Preparation of Sample Solutions of XANADOX 6000

Experiments were conducted to ascertain the medium and long term stability of XANADOX 6000 (6000 ppm) hypochlorous acid solutions. Both mixed bed quality deionised water (nil chloride content) and Daventry towns mains water (approx. 80 ppm as $Cl^-$) were used to assess relative stability.

A graduated 5 liter beaker was filled with 4.7 liters of water and 49 gm of SHOCK (Calcium hypochlorite ULC grade—Lonza Inc) was slowly added. Stirring was effected with a magnetic stirrer until a cloudy white dispersion appeared evenly distributed, and no solid material on the base of the container.

36.8 gm of sodium carbonate (Alfa Aesar, anhydrous 99.5% purity, chloride 0.001%) was added slowly with stirring. A white calcium carbonate precipitate was produced. The magnetic stirrer was switched off and the calcium carbonate was allowed to settle to the bottom of the beaker. After approx., two hours the clear supernatant liquid was filtered through a 1 micron filter bag.

The resulting clear solution was poured into nine 500 ml HD polythene sample bottles. Each 500 ml aliquot was added to a 1000 ml beaker with a magnetic stirrer. A pH probe (connected to a pH meter) was suspended in the 500 ml sodium hypochlorite solution.

98% Sulphuric acid (Analar Normapur) was carefully added by drop pipette to three of the 500 ml aliquots with the aim of achieving the following pH readings—5.5, 4.5, 3.5.

81% Phosphoric acid (FG—Food Grade) was added carefully by drop pipette to another three 500 ml aliquots with the aim of achieving the following pH readings—5.5, 4.5, 3.5.

68-70% Nitric acid (Alfa Aesar, Cl—0.5 ppm MAX) was added to the remaining three 500 ml aliquots with the aim of achieving the following pH readings—5.5, 4.5, 3.5.

Daventry Towns Mains water was used to make samples 590-598.

The following Table 10 gives the addition of 98% sulphuric acid, 81% phosphoric acid and 70% nitric acid to achieve the desired pH values.

TABLE 10

| | SAMPLE NO. | | |
|---|---|---|---|
| | 590 | 591 | 592 |
| 98% sulphuric acid added (gm) | 3.13 | 3.23 | 3.50 |
| Initial pH achieved | 5.40 | 4.33 | 3.50 |

| | SAMPLE NO. | | |
|---|---|---|---|
| | 593 | 594 | 595 |
| 81% phosphoric acid added (gm) | 6.98 | 7.86 | 8.05 |
| Initial pH achieved | 5.55 | 4.38 | 3.58 |

| | SAMPLE NO. | | |
|---|---|---|---|
| | 596 | 597 | 598 |
| 68-70% nitric acid added (gm) | 5.68 | — | 5.84 |
| Initial pH achieved | 5.55 | — | 3.72 |

Sample 597 was omitted from experimentation because of lack of aliquot sample.

The following results in Table 11 were taken over a six month period:

Table 11 below charts the change in ORP, pH and oxidant concentration since DATE OF PRODUCTION 22 Oct. 2013.

TABLE 11

| | Sample No. | | | | | | | |
|---|---|---|---|---|---|---|---|---|
| | 590 | 591 | 592 | 593 | 594 | 595 | 596 | 598 |
| DATE 24 Oct. 2013 Towns Mains Water | | | | | | | | |
| ORP | 1242 | 1238 | 1239 | 1204 | 1216 | 1226 | 1243 | 1242 |
| pH | 3.52 | 3.47 | 3.37 | 3.91 | 3.73 | 3.53 | 3.39 | 3.29 |
| [$Cl_2$] | 7161 | 7445 | 7515 | 6594 | 7374 | 7515 | 7090 | 7445 |
| DATE 30 Jan. 2014 Towns Mains Water | | | | | | | | |
| ORP | 1236 | 1238 | 1238 | 1221 | 1228 | 1226 | 1247 | 1251 |
| pH | 3.30 | 3.28 | 3.26 | 3.52 | 3.42 | 3.38 | 3.16 | 3.13 |
| [$Cl_2$] | 6310 | 6594 | 6665 | 5672 | 6310 | 6381 | 6310 | 6594 |
| DATE 1 Apr. 2014 Towns Mains Water | | | | | | | | |
| ORP | 1256 | 1252 | 1250 | 1231 | 1244 | 1242 | 1250 | 1255 |
| pH | 3.20 | 3.17 | 3.15 | 3.40 | 3.30 | 3.26 | 3.08 | 3.00 |
| [$Cl_2$] | 5530 | 6168 | 6310 | 5105 | 5885 | 6097 | 5814 | 6239 |

Mixed bed deionised water was used to make samples 600-608.

The following Table 12 gives the addition of 98% sulphuric acid, 81% phosphoric acid and 70% nitric acid to achieve the desired pH values.

TABLE 12

| | SAMPLE NO. | | |
|---|---|---|---|
| | 600 | 601 | 602 |
| 98% sulphuric acid added (gm) | 3.05 | 3.16 | 3.09 |
| Initial pH achieved | 5.54 | 4.42 | 3.50 |

TABLE 12-continued

| | SAMPLE NO. | | |
|---|---|---|---|
| | 603 | 604 | 605 |
| 81% phosphoric acid added (gm) | 6.84 | 7.44 | 7.71 |
| Initial pH achieved | 5.50 | 4.56 | 3.52 |

| | SAMPLE NO. | | |
|---|---|---|---|
| | 606 | 607 | 608 |
| 68-70% nitric acid added (gm) | 5.43 | 5.56 | 5.59 |
| Initial pH achieved | 5.43 | 4.50 | 3.36 |

Table 13 below charts the change in ORP, pH and oxidant concentration since DATE OF PRODUCTION 24 Oct. 2013.

TABLE 13

| | Sample No. | | | | | | | | |
|---|---|---|---|---|---|---|---|---|---|
| | 600 | 601 | 602 | 603 | 604 | 605 | 606 | 607 | 608 |
| DATE 26 Oct. 2013 Mixed bed deionised Water | | | | | | | | | |
| ORP | 1233 | 1233 | 1236 | 1197 | 1207 | 1224 | 1246 | 1245 | 1249 |
| pH | 3.57 | 3.48 | 3.37 | 3.94 | 3.75 | 3.47 | 3.39 | 3.33 | 3.24 |
| [Cl$_2$] | 7019 | 7232 | 7303 | 6381 | 7161 | 7161 | 7019 | 7303 | 7232 |
| DATE 30 Jan. 2014 Mixed bed deionised Water | | | | | | | | | |
| ORP | 1252 | 1245 | 1240 | 1222 | 1229 | 1234 | 1247 | 1249 | 1251 |
| pH | 3.45 | 3.41 | 3.36 | 3.60 | 3.48 | 3.41 | 3.25 | 3.23 | 3.18 |
| [Cl$_2$] | 6168 | 6381 | 6523 | 5530 | 6097 | 6310 | 6168 | 6381 | 6452 |
| DATE 1 Apr. 2014 Mixed bed deionised Water | | | | | | | | | |
| ORP | 1241 | 1244 | 1244 | 1226 | 1232 | 1236 | 1251 | 1254 | 1255 |
| pH | 3.26 | 3.22 | 3.18 | 3.45 | 3.34 | 3.28 | 3.05 | 2.98 | 2.99 |
| [Cl$_2$] | 5743 | 6027 | 6097 | 5176 | 5601 | 5885 | 5743 | 5814 | 5956 |

Findings from 1C and 1D

From the above results for XANADOX 8000 & XANADOX 6000, it would appear that there is no advantage in using mixed bed quality water which has a finite expense to produce, over the use of ordinary Daventry Towns Mains water. It was therefore decided only to prepare solutions based on Daventry Towns Mains water for all future preparations.

1E. Preparation of Sample Solutions of XANADOX 4000

Experiments were conducted to ascertain the medium and long term stability of XANADOX 4000 (4000 ppm) hypochlorous acid solutions.

A graduated 5 liter beaker was filled with 5.0 liters of water and 35 gm of SHOCK (Calcium hypochlorite ULC grade—Lonza Inc) was slowly added. Stirring was effected with a magnetic stirrer until a cloudy white dispersion appeared evenly distributed, and no solid material on the base of the container.

25.8 gm of sodium carbonate (Alfa Aesar, anhydrous 99.5% purity, chloride 0.001%) was added slowly with stirring. A white calcium carbonate precipitate was produced. The magnetic stirrer was switched off and the calcium carbonate was allowed to settle to the bottom of the beaker. After approx. two hours the clear supernatant liquid was filtered through a 1 micron filter bag.

The resulting clear solution was poured into nine 500 ml HD polythene sample bottles. Each 500 ml aliquot was added to a 1000 ml beaker with a magnetic stirrer. A pH probe (connected to a pH meter) was suspended in the 500 ml sodium hypochlorite solution.

98% Sulphuric acid (Analar Normapur) was carefully added by drop pipette to three of the 500 ml aliquots with the aim of achieving the following pH readings—5.5, 4.5, 3.5.

81% Phosphoric acid (FG—Food Grade) was added carefully by drop pipette to another three 500 ml aliquots with the aim of achieving the following pH readings—4.5, 5.0, 5.0.

68-70% Nitric acid (Alfa Aesar, Cl—0.5 ppm MAX) was added to the remaining three 500 ml aliquots with the aim of achieving the following pH readings—5.5, 4.5, 3.5.

Daventry Towns Mains water was used to make samples 610-618.

The following Table 14 gives the addition of 98% sulphuric acid, 81% phosphoric acid and 70% nitric acid to achieve the desired pH values.

TABLE 14

| | SAMPLE NO. | | |
|---|---|---|---|
| | 610 | 611 | 612 |
| 98% sulphuric acid added (gm) | 1.96 | 1.97 | 1.98 |
| Initial pH achieved | 5.52 | 4.34 | 3.63 |

| | SAMPLE NO. | | |
|---|---|---|---|
| | 613 | 614 | 615 |
| 81% phosphoric acid added (gm) | 4.43 | 4.93 | 4.91 |
| Initial pH achieved | 5.53 | 4.48 | 3.61 |

| | SAMPLE NO. | | |
|---|---|---|---|
| | 616 | 617 | 618 |
| 68-70% nitric acid added (gm) | 3.57 | 3.65 | 3.64 |
| Initial pH achieved | 5.47 | 4.24 | 3.32 |

Table 15 below charts the change in ORP, pH and oxidant concentration since DATE OF PRODUCTION 26 Oct. 2013.

TABLE 15

| | Sample No. | | | | | | | |
|---|---|---|---|---|---|---|---|---|
| 610 | 611 | 612 | 613 | 614 | 615 | 616 | 617 | 618 |
| DATE 29 Oct. 2013 Daventry Towns Mains Water | | | | | | | | |
| ORP 1239 | 1237 | 1241 | 1206 | 1217 | 1230 | 1241 | 1242 | 1250 |
| pH 3.68 | 3.56 | 3.48 | 4.01 | 3.83 | 3.56 | 3.47 | 3.39 | 3.24 |
| [Cl$_2$] 4892 | 4892 | 4963 | 4538 | 4892 | 4750 | 4750 | 4963 | 5034 |
| DATE 30 Jan. 2014 Daventry Towns Mains Water | | | | | | | | |
| ORP 1232 | 1235 | 1235 | 1223 | 1227 | 1229 | 1238 | 1238 | 1241 |
| pH 3.51 | 3.44 | 3.43 | 3.62 | 3.54 | 3.47 | 3.36 | 3.30 | 3.28 |
| [Cl$_2$] 4396 | 4467 | 4538 | 4112 | 4325 | 4538 | 4396 | 4467 | 4467 |
| DATE 7 Apr. 2014 Daventry Towns Mains Water | | | | | | | | |
| ORP 1234 | 1235 | 1236 | 1223 | 1229 | 1231 | 1244 | 1246 | 1246 |
| pH 3.33 | 3.30 | 3.30 | 3.47 | 3.38 | 3.35 | 3.21 | 3.17 | 3.15 |
| [Cl$_2$] 4041 | 4183 | 4112 | 3758 | 4041 | 4041 | 4041 | 4183 | 4183 |
| DATE 18 Aug. 2014 Daventry Towns Mains Water | | | | | | | | |
| ORP 1253 | 1253 | 1252 | 1234 | 1241 | 1243 | 1254 | 1257 | 1259 |
| pH 3.08 | 3.10 | 3.10 | 3.31 | 3.18 | 3.20 | 2.99 | 2.93 | 2.84 |
| [Cl$_2$] 3190 | 3403 | 3510 | 3013 | 3155 | 3403 | 3332 | 3439 | 3368 |

Results

The invention provides a two-step method of manufacturing an aqueous low chloride solution of principally hypochlorous acid having a pH between 3.0 and 6.0 and a stability such that after 6 months storage at 20 degrees Celsius the pH remains in the range 3.0 to 6.0 and the redox potential remains above 1000 mV.

When producing hypochlorous acid solutions with >2000 ppm as free chlorine, there is no discernible difference between using solutions prepared with mixed bed deionised water quality compared to Daventry Towns Mains water. It would be expected that the contribution of 80 ppm of chloride from the Mains water would increase the rate of decay of oxidant—but this is not found to be the case. Hence a considerable cost saving can be made in both capital expenditure and running costs by not having to invest in a sophisticated water treatment plant.

It was observed that sulphuric acid produces solutions have lower rates of decay of produced oxidant.

With all three strong acids used, acidification of the sodium hypochlorite solutions has an optimum pH of approx 3.20-3.50 for production of hypochlorous acid solutions. The solutions at this initial pH range are more stable to decay, and they have higher ORP values which makes them more effective for biocidal action.

After approximately six months of storage, the best solutions with high oxidant levels and high ORP levels still have an oxidant level near to that indicated by the product label. After approximately twenty four months of storage, the best solutions with high oxidant levels and high ORP levels still have an oxidant level near to that indicated by the product label.

Example 2—Production of Hypochlorous Acid Solutions with Very High ORP Levels

2A. Preparation of Hypochlorous Acid Solution Via Known Method Followed by Treatment with Lead Nitrate In this experiment, an initial aqueous solution of hypochlorous acid was produced using a known method based on simple acidification of calcium hypochlorite with nitric acid. This was followed by a treatment with lead nitrate.

The following experiment was conducted to prepare a 1 liter sample of 5000 ppm HOCl solution.

A graduated 2 liter beaker was filled with 1.0 liters of Daventry Towns Mains water and 8.0 gm of calcium hypochlorite LC grade—Lonza Inc) was slowly added. Stirring was effected with a magnetic stirrer until a cloudy white dispersion appeared evenly distributed. A pH probe (connected to a pH meter) was suspended in the solution and nitric acid (50%) was added carefully by drop pipette until a pH of 5.8 was reached. 2.6 g of lead nitrate crystals were sprinkled into the solution and a white cloudy precipitate was produced. It was observed that the pH of the solution dropped by 1 unit.

The white precipitate quickly sank to the bottom of the beaker. On leaving overnight the white precipitate turned black and there was a further drop in pH. The solution was filtered through a Whatman No. 1 filter disc.

Without wishing to be bound by theory, it is thought that the drop in pH was due to the following reaction:

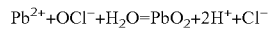

$$Pb^{2+}+OCl^-+H_2O=PbO_2+2H^++Cl^-$$

It is thought that the black precipitate was due to the formation of insoluble lead oxide.

The following table 16 shows the solution parameters over a two year period.

TABLE 16

HOCL 5000 ppm PREPARATION DATE 24 May 2011

| | DATE | | | | | | | | |
|---|---|---|---|---|---|---|---|---|---|
| | 14 Jun. 2011 | 6 Jul. 2011 | 16 Sep. 2011 | 18 Oct. 2011 | 14 Feb. 2012 | 17 May 2012 | 4 Oct. 2012 | 8 Oct. 2012 | 12 Apr. 2013 |
| ORP | >1000 | 1276 | 1274 | 1265 | 1230 | 1280 | 1303 | 1288 | 1290 |
| pH | 2.00 | 1.93 | 1.98 | 1.89 | 1.99 | 1.69 | 2.16 | 2.00 | 2.22 |
| [Cl$_2$] DPD | 5000 | 4500 | 3500 | 3500 | 3000 | 3000 | 2500 | * | * |
| [Cl$_2$] Titration | **__ | **__ | **__ | **__ | 3190 | 2978 | 2623 | 2623 | 2340 |

\* DPD determination not done once total oxidant concentration measured.
\*\*— During 2011, total oxidant concentration not determined.

Hence over a two year period the oxidant level had decayed to just under half, but the ORP level was at a high level with a lower pH.

2B. Preparation of XANADOX 5500 Solutions from Daventry Towns Mains Water and Calcium Carbonate Precipitation, Followed by Insoluble Lead Compound Precipitation In this experiment, an initial aqueous solution of hypochlorous acid was produced using a method according to the first aspect of the invention, based on treatment of calcium hypochlorite with sodium carbonate and precipation of calcium carbonate, with subsequent pH adjustment with phosphoric acid. This was followed by a treatment with lead nitrate.

A graduated 5 liter beaker was filled with 3.75 liters of water and 36 gm of SHOCK (Calcium hypochlorite ULC grade—Lonza Inc) was slowly added. Stirring was effected with a magnetic stirrer until a cloudy white dispersion appeared evenly distributed, and no solid material on the base of the container.

26.9 gm of sodium carbonate (Alfa Aesar, anhydrous 99.5% purity, chloride 0.001%) was added slowly with stirring. A white calcium carbonate precipitate was produced. The magnetic stirrer was switched off and the calcium carbonate was allowed to settle to the bottom of the beaker. After approx. two hours the clear supernatant liquid was filtered through a 1 micron filter bag.

The resulting clear solution was poured into a clean 5 liter beaker with a magnetic stirrer. A pH probe (connected to a pH meter) was suspended in the solution.

81% Phosphoric acid (FG—Food Grade) was added carefully by drop pipette until a pH of 5.6 was attained (46.1 gm added).

The resulting clear solution was poured into seven 500 ml HD polythene sample bottles and sealed with closures.

Increasing amounts of lead nitrate crystals were weighed out on a balance and added to each 500 ml aliquot with magnetic stirring. The clear solutions turned immediately to give an insoluble white dispersion. The solutions were left overnight and then filtered with Whatman No. 1 filter discs.

TABLE 17

DATE OF PREPARATION 14 Mar. 2013

| | SAMPLE NO. (500 ml) | | | | | | |
|---|---|---|---|---|---|---|---|
| | 380 | 381 | 382 | 383 | 384 | 385 | 386 |
| 81% phosphoric acid added (gm) | | | | 46.1 gm | | | |
| Amount of lead nitrate added (gm) | 0 | 1.25 | 2.50 | 3.75 | 5.0 | 6.25 | 7.5 |

The clear solutions were then stored over a 12 month period and the following parameters recorded.

TABLE 18

DATE 14 Mar. 2013 Daventry Towns Mains Water

| | | DATE | | | |
|---|---|---|---|---|---|
| | | 15 Mar. 2013 | 18 Apr. 2013 | 9 Aug. 2013 | 4 Mar. 2014 |
| SAMPLE NO. 380 | ORP | 1159 | 1219 | 1240 | 1232 |
| | pH | 4.50 | 3.64 | 3.38 | 3.35 |
| | [Cl$_2$] | 6452 | 6026 | 4750 | 3474 |
| SAMPLE NO. 381 | ORP | 1186 | 1227 | 1244 | 1244 |
| | pH | 4.01 | 3.47 | 3.21 | 3.11 |
| | [Cl$_2$] | 7019 | 6452 | 4963 | 3687 |
| SAMPLE NO. 382 | ORP | 1234 | 1242 | 1252 | 1256 |
| | pH | 3.14 | 3.12 | 3.02 | 2.92 |
| | [Cl$_2$] | 6948 | 6594 | 5318 | 4112 |
| SAMPLE NO. 383 | ORP | 1259 | 1260 | 1262 | 1269 |
| | pH | 2.69 | 2.76 | 2.76 | 2.71 |
| | [Cl$_2$] | 6948 | 6594 | 5530 | 4467 |
| SAMPLE NO. 384 | ORP | 1272 | 1271 | 1271 | 1277 |
| | pH | 2.44 | 2.51 | 2.54 | 2.50 |
| | [Cl$_2$] | 6877 | 6665 | 5743 | 4885 |
| SAMPLE NO. 385 | ORP | 1287 | 1281 | 1278 | 1288 |
| | pH | 2.23 | 2.31 | 2.35 | 2.32 |
| | [Cl$_2$] | 7019 | 6665 | 5885 | 5247 |
| SAMPLE NO. 386 | ORP | 1293 | 1287 | 1284 | 1294 |
| | pH | 2.06 | 2.13 | 2.19 | 2.15 |
| | [Cl$_2$] | 6948 | 6736 | 6027 | 5530 |

It can be clearly seen that the following trends are highlighted as the amount of lead nitrate is increased.
(1) With each sample the pH of solution decreases or remains the same over the 12 month period.
(2) The oxidant level decreases in every sample over the twelve month period but the rate of decrease slows as the concentration of added lead nitrate increases.
(3) The ORP levels increase & the pH decreases with the higher concentration of lead nitrate added.

Hence the common trend is that the more lead nitrate added, the more stable and more powerful the solution becomes.

The chemistry involved has not yet been fully elucidated. It had been assumed that the white precipitate produced would be lead phosphate, but without wishing to be bound by theory, something more complex must be taking place to achieve lower pH values.

An important advantage of using calcium carbonate precipitation, filtration, and phosphoric acid addition followed by lead nitrate addition is that a clean white precipitate is produced, which can be easily filtered off to give clear solutions and uncontaminated process equipment.

It was found that when sulphuric acid was used as the neutralising acid and lead nitrate was added to the hypochlorous acid solutions, no drop in pH occurred and no enhanced ORP levels were detected. This result was to be expected because lead sulphate is very insoluble.

2C. Preparation of XANADOX 8000 Solutions from Daventry Towns Mains Water and Calcium Carbonate Precipitation, Followed by Insoluble Lead Compound Precipitation In this experiment, an initial aqueous solution of hypochlorous acid was produced using a method according to the first aspect of the invention, based on treatment of calcium hypochlorite with sodium carbonate and precipitation of calcium carbonate, with subsequent pH adjustment with phosphoric acid. This was followed by a treatment with lead nitrate.

A graduated 5 liter beaker was filled with 3.75 liters of water and 52.5 gm of SHOCK (calcium hypochlorite ULC grade—Lonza Inc) was slowly added. Stirring was effected with a magnetic stirrer until a cloudy white dispersion appeared evenly distributed, and no solid material on the base of the container.

39.0 gm of sodium carbonate (Alfa Aesar, anhydrous 99.5% purity, chloride 0.001%) was added slowly with stirring. A white calcium carbonate precipitate was produced. The magnetic stirrer was switched off and the calcium carbonate was allowed to settle to the bottom of the beaker. After approx. two hours the clear supernatant liquid was filtered through a 1 micron filter bag.

The resulting clear solution was poured into a clean 5 liter beaker with a magnetic stirrer. A pH probe (connected to a pH meter) was suspended in the solution.

81% Phosphoric acid (FG—Food Grade) was added carefully by drop pipette until a pH of 5.6 was attained (66.5 gm added).

The resulting clear solution was poured into seven 500 rill HD polythene sample bottles and sealed with closures.

Increasing amounts of lead nitrate crystals were weighed out on a balance and added to each 500 ml aliquot with magnetic stirring. The clear solutions turned immediately to give an insoluble white dispersion. The solutions were left overnight and then filtered with Whatman No. 1 filter discs.

TABLE 19

DATE OF PREPARATION 15 Mar. 2013

| | SAMPLE NO. (500 ml) | | | | | | |
|---|---|---|---|---|---|---|---|
| | 390 | 391 | 392 | 393 | 394 | 395 | 396 |
| 81% phosphoric acid added (gm) | | | | 66.5 gm | | | |
| Amount of lead nitrate added (gm) | 0 | 1.83 | 3.66 | 5.50 | 7.33 | 9.16 | 11.0 |

The clear solutions were then stored over a 12 month period and the following parameters recorded.

TABLE 20

| | | DATE | | | | | | | |
|---|---|---|---|---|---|---|---|---|---|
| | | 16 Mar. 2013 | 19 Apr. 2013 | 23 May 2013 | 5 Jul. 2013 | 16 Aug. 2013 | 17 Oct. 2013 | 25 Nov. 2013 | 14 Mar. 2014 |
| 390 | ORP | 1203 | 1236 | 1225 | 1252 | 1242 | 1237 | 1260 | 1243 |
| | pH | 4.50 | 3.60 | 3.44 | 3.25 | 3.14 | 3.07 | 3.17 | 3.04 |
| | [Cl2] | 9501 | 8012 | 7302 | 6239 | 5388 | 5034 | 4750 | 4467 |
| 391 | ORP | 1209 | 1237 | 1236 | 1260 | 1251 | 1247 | 1259 | 1250 |
| | pH | 3.96 | 3.40 | 3.25 | 3.09 | 2.96 | 2.88 | 2.95 | 2.81 |
| | [Cl2] | 9572 | 8579 | 7728 | 6665 | 5743 | 5105 | 4679 | 4041 |
| 392 | ORP | 1241 | 1245 | 1243 | 1267 | 1256 | 1255 | 1265 | 1260 |
| | pH | 3.29 | 3.20 | 3.08 | 2.96 | 2.87 | 2.79 | 2.86 | 2.72 |
| | [Cl2] | 9855 | 9146 | 8295 | 7303 | 6523 | 6027 | 5530 | 4892 |
| 393 | ORP | 1263 | 1259 | 1259 | 1278 | 1265 | 1266 | 1273 | 1273 |
| | pH | 2.74 | 2.82 | 2.79 | 2.71 | 2.68 | 2.62 | 2.72 | 2.57 |
| | [Cl2] | 9855 | 9146 | 8579 | 7728 | 6736 | 6168 | 5814 | 5459 |
| 394 | ORP | 1274 | 1272 | 1272 | 1287 | 1274 | 1276 | 1283 | 1285 |
| | pH | 2.43 | 2.53 | 2.53 | 2.46 | 2.46 | 2.42 | 2.52 | 2.40 |
| | [Cl2] | 9713 | 9217 | 8720 | 7870 | 7161 | 6594 | 6239 | 5743 |
| 395 | ORP | 1289 | 1284 | 1284 | 1297 | 1284 | 1286 | 1293 | 1297 |
| | pH | 2.14 | 2.26 | 2.26 | 2.21 | 2.22 | 2.19 | 2.33 | 2.20 |
| | [Cl2] | 9642 | 9288 | 8863 | 8295 | 7870 | 7302 | 6877 | 6523 |
| 396 | ORP | 1298 | 1292 | 1293 | 1304 | 1292 | 1294 | 1300 | 1306 |
| | pH | 1.95 | 2.08 | 2.06 | 2.02 | 2.03 | 1.99 | 2.14 | 2.03 |
| | [Cl2] | 9713 | 9430 | 9146 | 8721 | 8154 | 7515 | 7161 | 6736 |

Again the same trends were apparent as with samples 380-386.

(1) With each sample the pH of solution decreases or remains the same over the 12 month period.
(2) The oxidant level decreases in every sample over the twelve month period but the rate of decrease slows as the concentration of added lead nitrate increases.
(3) The ORP levels increase & the pH levels decrease with the higher concentration of lead nitrate added.

Hence the common trend is that the more lead nitrate added, the more stable and more powerful the solution becomes.

It was also found that increasing the quantities of lead even more increased the ORP levels to as high as 1330 mV but the pH values decreased accordingly. It was not considered economical to use higher lead nitrate levels.

It is also possible to collect & recycle the precipitated lead phosphate complex and it can be converted back to lead nitrate for reuse. Hence there would be no environmental impact in using lead nitrate.

Hypochlorous acid solutions prepared by known methods based on calcium phosphate precipitation have also been subject to lead nitrate addition. Although some satisfactory solutions can be produced with white precipitate, higher concentration solutions always yield black lead oxide precipitation which is not desired.

Results

Powerful oxidising solutions of hypochlorous acid can be produced using the calcium carbonate precipitation reaction followed by phosphoric acid pH correction. When these solutions are subject to the addition of lead nitrate, insoluble lead phosphate complexes are produced which can be removed by filtration leaving even more powerful hypochlorous acid solutions which have very high oxidation reduction potentials (ORPs).

The invention claimed is:

1. A process for preparing an aqueous solution comprising hypochlorous acid, the process comprising:
   i. treating an aqueous starting solution comprising hypochlorite and a precipitable counter-ion with an alkali metal carbonate to form a counter-ion precipitate and a supernatant liquid having a pH greater than 6.0;
   ii. removing at least part of said precipitate; and subsequently
   iii. acidifying at least part of the supernatant liquid with a strong inorganic acid other than hydrochloric acid, to a pH in the range of from 3.0 to 6.0, to form an aqueous product solution comprising hypochlorous acid.

2. The process of claim 1, wherein the starting solution comprises a hypochlorite salt component dissolved in an aqueous medium.

3. The process of claim 2 wherein the hypochlorite salt component comprises calcium hypochlorite.

4. The process of claim 2, wherein the hypochlorite salt component comprises commercial grade hypochlorite having an assay purity of at least 70% w/w.

5. The process of claim 2 wherein the aqueous medium comprises mains water.

6. The process of claim 1, wherein the alkali al carbonate comprises sodium carbonate.

7. The process of claim 1, wherein (ii) comprises allowing the precipitate to settle, pumping away a slurry comprising the settled precipitate; and optionally filtering the precipitate from the slurry.

8. The process of claim 1, wherein the strong inorganic acid is chosen from nitric acid, sulphuric acid, phosphoric acid, and mixtures thereof.

9. The process of claim 8 wherein the strong inorganic acid comprises sulphuric acid.

10. The process of claim 1, wherein the supernatant liquid is acidified to a pH in the range of from 3.0 to 3.5.

11. The process of claim 1 comprising treating the product solution with lead nitrate, to form a lead-based precipitate; and removing at least a part of said lead-based precipitate.

12. A process for preparing an aqueous solution comprising hypochlorous acid, the process comprising:
   i. treating an aqueous starting solution comprising calcium or magnesium hypochlorite with an alkali metal carbonate to form a precipitate and a supernatant liquid;
   ii. removing at least part of said precipitate; and subsequently
   iii. acidifying at least part of the supernatant liquid with a strong inorganic acid other than hydrochloric acid, to a pH in the range of from 3.0 to 6.0, to form an aqueous product solution comprising hypochlorous acid.

* * * * *